(12) United States Patent
Potyrailo et al.

(10) Patent No.: US 8,936,191 B2
(45) Date of Patent: Jan. 20, 2015

(54) FIELD-PORTABLE IMPEDANCE READER AND METHODS OF MAKING THE SAME

(75) Inventors: Radislav Alexandrovich Potyrailo, Niskayuna, NY (US); Jeffrey Michael Ashe, Gloversville, NY (US); William Guy Morris, Rexford, NY (US); Cheryl Margaret Surman, Guilderland, NY (US)

(73) Assignee: General Electric Company, Niskayuna, NY (US)

( * ) Notice: Subject to any disclaimer, the term of this patent is extended or adjusted under 35 U.S.C. 154(b) by 1240 days.

(21) Appl. No.: 12/827,623

(22) Filed: Jun. 30, 2010

(65) Prior Publication Data

US 2012/0004851 A1 Jan. 5, 2012

(51) Int. Cl.
*G06K 5/00* (2006.01)

(52) U.S. Cl.
USPC .......................................... 235/380; 235/382

(58) Field of Classification Search
CPC .. G06K 7/10881; G06K 7/0008; G06K 7/086
USPC ............................ 235/472.01, 472.02, 462.45
See application file for complete search history.

(56) References Cited

U.S. PATENT DOCUMENTS

| 5,157,338 | A | 10/1992 | Motherbaugh et al. |
| 7,445,143 | B2 | 11/2008 | Pang et al. |
| 2004/0113790 | A1* | 6/2004 | Hamel et al. ............... 340/572.1 |
| 2005/0022581 | A1 | 2/2005 | Sunshine |
| 2007/0090926 | A1 | 4/2007 | Potyrailo et al. |
| 2007/0090927 | A1 | 4/2007 | Potyrailo et al. |
| 2008/0180249 | A1* | 7/2008 | Butler et al. ............... 340/572.1 |
| 2009/0278685 | A1* | 11/2009 | Potyrailo et al. ........... 340/572.1 |
| 2009/0289776 | A1* | 11/2009 | Moore et al. ............... 340/10.41 |
| 2011/0248825 | A1* | 10/2011 | Hamel et al. ................. 340/10.1 |

FOREIGN PATENT DOCUMENTS

| WO | 2007101992 A1 | 9/2007 |
| WO | 2007139574 A1 | 12/2007 |

OTHER PUBLICATIONS

Richard D Yang; Bernd Fruhberger; Jeongwon Park and Andrew Kummel; "Chemical identification using an impedance sensor based on dispersive charge transport"; Applied Physics Letters, vol. 88, Issue 7, id. 074104 (2006); http://adsabs.harvard.edu/abs/2006ApPhL..88g4104Y; 2 Pages.

Xiang-Hong Wang and Shuo Wang; "Sensors and Biosensors for the Determination of Small Molecule Biological Toxins"; Sensors 2008, 8, 6045-6054; DOI: 10.3390/s8096045; in revised form: Sep. 3, 2008 / Accepted: Sep. 5, 2008 /Published: Sep. 26, 2008; http://www.mdpi.com/1424-8220/8/9/6045/pdf; 10 Pages.

Osse F, Lukas R, Zhou R, Schneider S and Everhart D; "AC-impedance-based chemical sensors for organic solvent vapors"; 1996, vol. 36, No. 1-3 (v-ix, 263-545 [289 p.]) (12 ref.), [Notes: Part. II], pp. 363-369; http://cat.inist.fr/?aModele=afficheN&cpsidt=2595178; 2 Pages.

(Continued)

*Primary Examiner* — Daniel St. Cyr
(74) *Attorney, Agent, or Firm* — Seema S. Katragadda

(57) ABSTRACT

A field-portable impedance reader is provided. The impedance reader comprises a reader antenna, an impedance compensator, a calibrator, and a synchronous sampler. The impedance reader further comprises a digital processor that receives and processes signals from the synchronous sampler. Further, a wireless system comprising the impedance reader of the invention is provided.

21 Claims, 10 Drawing Sheets

(56) References Cited

OTHER PUBLICATIONS

Amrani et al ; High-frequency measurements of conducting polymers: development of a new technique for sensing volatile chemicals; http://iopscience.iop.org/0957-0233/6/10/010; 8 Pages.

Amrani and Payne; ; "Multi-frequency interrogation technique applied to conducting polymer gas and odour sensors"; INSPEC Accession No. 6227404; Issue Date: Mar. 1999; INSPEC Accession No. 6227404; ISSN: 1350-2344 ; 2 Pages.

Wise KD and Najafi K; Microfabrication techniques for integrated sensors and microsystem; http://www.ncbi.nlm.nih.gov/pubmed/1962192; 1 Page.

Aimée Rose, Zhengguo Zhu, Conor F. Madigan, Timothy M. Swager and Vladimir Bulovi; "Sensitivity gains in chemosensing by lasing action in organic polymers"; Nature 434, 876-879 (Apr. 14, 2005) | doi:10.1038/nature03438; Accepted Feb. 4, 2005; http://www.nature.com/nature/journal/v434/n7035/full/nature03438.html; 8 Pages.

Potyrailo, Radislav A., et al., "Integration of Passive Multivariable RFID Sensors Into Single-Use Biopharmaceutical Manufacturing Components," 2010 IEEE International Conference on RFID, Apr. 14, 2010, pp. 1-7, USA.

EP Search Report and Written Opinion dated Mar. 5, 2014, issued in connection with corresponding EP Patent Application No. 11801238.4.

Radislav Alexandrovich Potyrailo et al.; "Integration of Passive Multivariable RFID Sensors Into Single-Use Biopharmaceutical Manufacturing Components"; 2010 IEEE International Conference on RFID, USA, Apr. 14, 2010; 7 Pages.

Radislav Alexandrovich Potyrailo et al.; "RFID sensors based on ubiquitous passive 13.56Mhz RFID tags and complex impedance detection"; Published online Nov. 27, 2008 in Wiley InterScience; 13 Pages.

Radislav Alexandrovich Potyrailo et al.; "Selective quantitation of vapors and their mixtures using individual passive multivariable RFID sensors"; 2010 IEEE International Conference on RFID, USA; 7 Pages.

WO search report attached; Application No. SE 2011/050818, Filed on Jun. 22, 2011.

EP search report attached; Application No. SE 11801238.4, Filed on Jan. 30, 2013.

\* cited by examiner

US 8,936,191 B2

FIELD-PORTABLE IMPEDANCE READER AND METHODS OF MAKING THE SAME

The U.S. Government has certain rights in this invention pursuant to National Institute of Environmental Health Sciences contract number 1R01ES016569-01A1.

BACKGROUND

The invention relates generally to resonant sensors, and more particularly to impedance readers for resonant sensors and methods of making such impedance readers.

Generally, RFID readers are used to obtain digital data from RFID tags. Digital data may include, for example, digital identification of the tag, or any other information written and/or stored in a memory chip of the RFID tag. The RFID tags transmit electromagnetic signals at different relative levels of transmitted power at different times. Signals received by the RFID reader in combination with the transmitted relative power level of the received signals are employed to locate the RFID tags, and read the digital identification information from the RFID tag (e.g., from the memory chip or back-reflector structure of the RFID tag).

Resonant sensors are used for sensing physical, chemical, and biological constituents in a sample. Examples of the resonant sensors may include RFID sensors, or LCR sensors, where L stands for inductor, C stands for capacitor, and R stands for resistor. The resonant sensors are cost-effective, and easy to incorporate in a component or a system for measuring physical, chemical or biological constituents of the component or the system.

Typically, analog or sensor data from the resonant sensors, such as the LCR sensors or the RFID sensors, is read using an impedance reader. Typically, passive RFID tags are used to make the RFID sensors because passive RFID tags are cost efficient as compared to active RFID tags. However, with the passive tags, the read range is influenced by frequency, reader output power, antenna design, and method of powering the RFID tags. In lab environment, bulky desktop-based laboratory reader systems are employed that need line power, limiting the applicability of the resonant sensors to lab environment. Hence, applications of such resonant sensors are limited by availability of the readers. Specifically, it may be difficult to provide a reader in field situations, or places outside a lab environment.

Therefore, it is desirable to have a field-portable impedance reader for the resonant sensors.

BRIEF DESCRIPTION

In one embodiment, a field-portable impedance reader is provided. The impedance reader comprises a reader antenna, an impedance compensator, a calibrator, a synchronous sampler, and a digital processor that receives and processes signals from the synchronous sampler.

In another embodiment, a wireless system comprising the impedance reader of the invention is provided.

In yet another embodiment, a field-portable impedance reader is provided. The impedance reader comprises a first layer comprising a reader antenna, a second layer comprising radio frequency electronics and intermediate frequency electronics, and a third layer comprising a digital direct synthesizer, a reference analog to digital converter, a sample analog to digital converter, and a digital signal processor, wherein the layers are disposed in a housing.

In another embodiment, a method for quantitating one or more of chemical, biological, or physical parameters in an environment is provided. The method comprises measuring a frequency-dependent impedance response of an LCR sensor across a resonance frequency, using a field-portable impedance reader, simultaneously calculating at least two univariate responses from the LCR sensor; analyzing using a multivariate analysis of the at least two univariate responses from the LCR sensor, and correlating results of the multivariate analysis to stored calibration values to provide quantitative values of the measured sensor responses to the parameter levels.

DRAWINGS

These and other features, aspects, and advantages of the invention will become better understood when the following detailed description is read with reference to the accompanying drawings in which like characters represent like parts throughout the drawings, wherein:

FIG. 6A is the measured Zp, and FIG. 6B is the measured Fp;

Figure 8A:
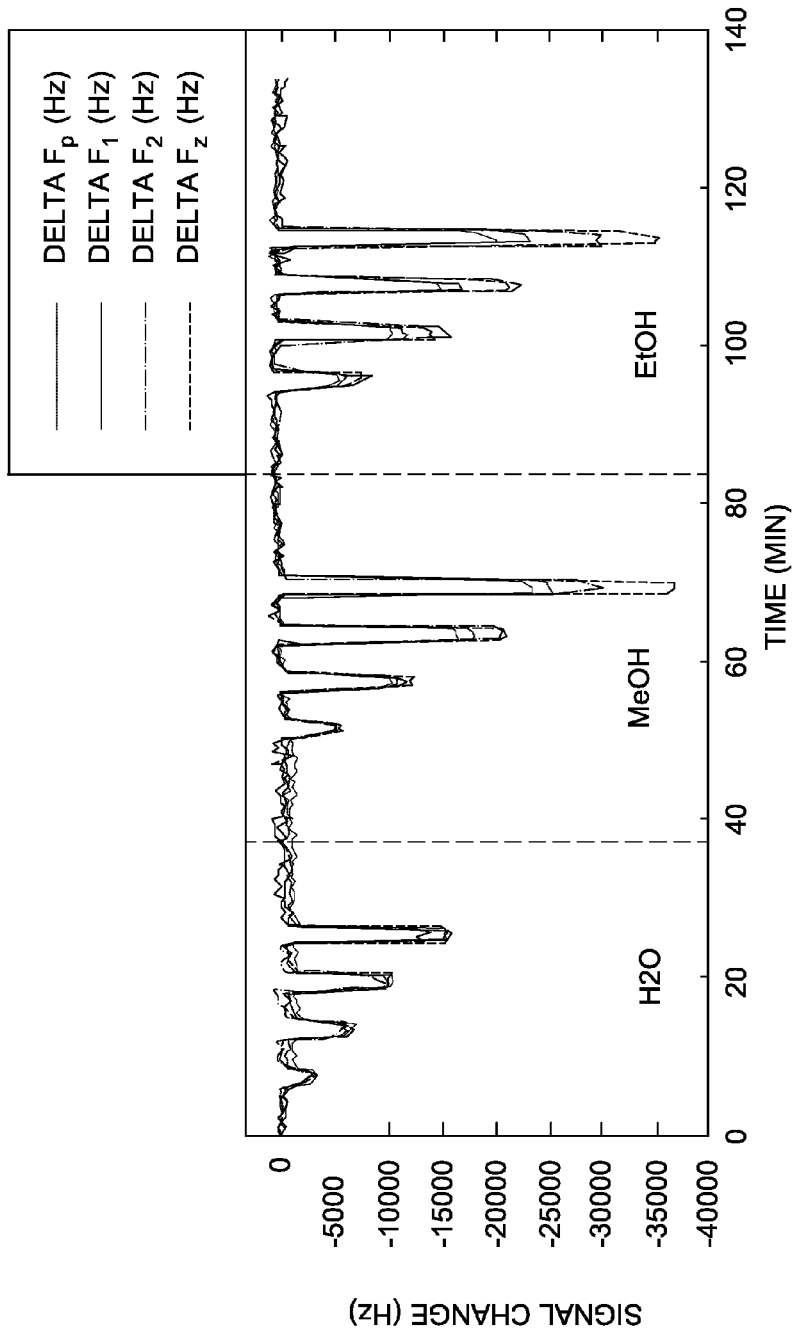
Figure 8B:
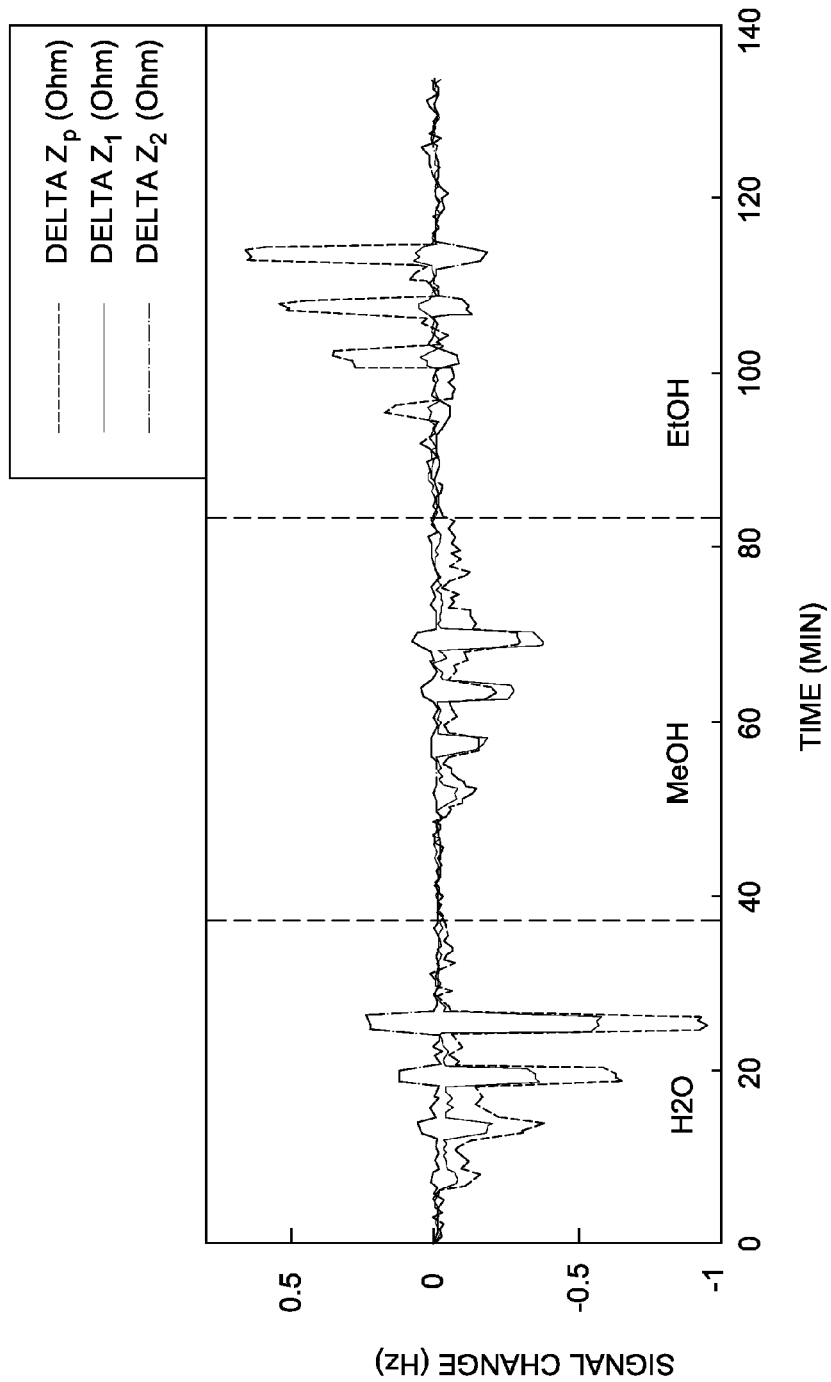
Figure 9B:
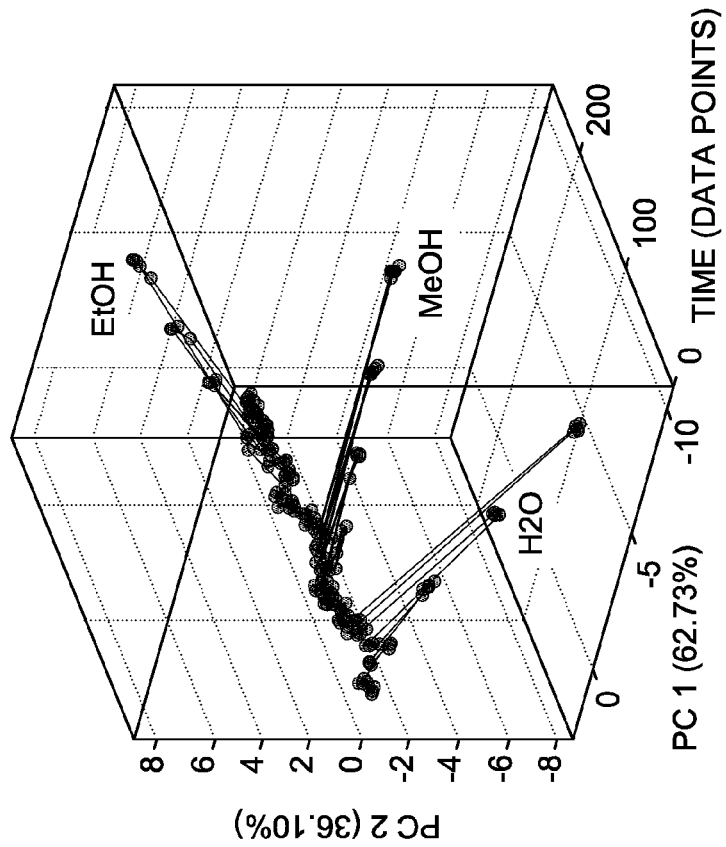
Figure 9A:
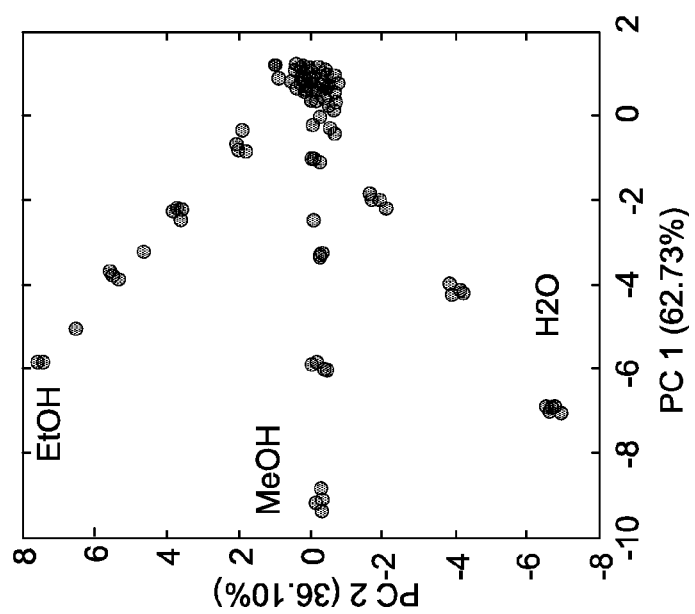

FIGS. 8A and 8B are graphs of operation example of the field-portable impedance reader of the invention that was used to conduct measurements from a single sensor that discriminated between three types of vapors, namely water, methanol and ethanol. FIG. 8A is simultaneous measurements of Fp, Fz, $F_1$, and $F_2$. FIG. 8B is simultaneous measurements of Zp, $Z_1$, and $Z_2$; and FIGS. 9A and 9B are scores plots from an example of a principal components analysis of an embodiment of a field-portable impedance reader that was used to conduct measurements from a single sensor that discriminated between three types of vapors, namely water, methanol and ethanol.

DETAILED DESCRIPTION

The embodiments disclosed herein relate to a portable field device for physical, chemical and/or biological detection using resonant sensors. In certain embodiments, a field-portable impedance reader is used to collect analog signals from a resonant sensor to obtain sensing data corresponding to the resonant sensor. The impedance reader measures impedance spectrum of a resonant sensor circuit of the resonant sensor. In one example, the field-portable impedance reader is a hand-held device.

As used herein, the term "resonant sensor" means a sensor that has an equivalent circuit that includes inductor (L), capacitor (C), and resistor (R) components. The L, C and R components in concert provide a resonant circuit that resonates at a given frequency. The resonant spectrum of the resonant circuit is affected by the changes in L, C, and R components of the circuit.

In one example, the resonant sensor may be a RFID sensor. The RFID sensor may comprise a memory chip. The memory chip may be used to store and retrieve data when required. The data may include a digital ID of the RFID sensor, or any other information of the RFID sensor. The memory chip may be a read-write chip, such as an integrated circuit (IC) chip. Alternatively, the memory chip may be a read-only chip, such as an acoustic wave device chip.

The resonant sensors may be used to measure a variety of physical, chemical and/or biological parameters. The sensors may be wireless resonant sensors or wired resonant sensors. The field-portable impedance reader is in operative association with the resonant sensor through the reader antenna. The wireless resonant sensors may be wirelessly coupled to the field-portable impedance reader. The wired resonant sensors may be electrically coupled using wires to the field-portable impedance reader or other components of the sensor system. In embodiments where the sensor is a wireless sensor, the impedance reader may be in communication with the reader antenna. In embodiments where the sensor is a wired sensor, the impedance reader may be in communication with the sensor. In one embodiment, the field-portable impedance reader monitors in real-time, and/or in a continuous fashion.

Two different approaches may be used for sensing. In one approach, a sensing material may be disposed on the reader antenna to alter the impedance response of the sensor. In another approach, a complementary sensor may be attached across an antenna and an optional memory chip. The complementary sensor may be used to alter sensor impedance response. Examples of such sensors are described in U.S. patent application Ser. No. 12/118,950, entitled "Methods and systems for calibration of RFID sensors", which is incorporated herein by reference.

In embodiments where the sensing material is disposed on the reader antenna, any changes in the sensing material may affect the sensor response. In one embodiment, an antenna is made in part from the sensing material that is responsive to environment. In this embodiment, the antenna is sensitive to the environment and may sense one or more of a chemical, biological or physical parameters.

By applying a sensing material onto the resonant antenna of the RFID tag and measuring the complex impedance of the RFID resonant antenna, impedance response may be correlated to the biological or chemical parameters. In certain embodiments, the sensitive material changes upon exposure to trace concentrations of an analyte. In these embodiments, the trace concentrations may be measured by disposing the sensing material between the electrodes that constitute the resonant circuit. Thus, dielectric, dimensional, charge transfer, and other changes in the properties of the sensing material may be detected by the changes in the resonant properties of the circuit.

Advantageously, a resonant sensor having the sensing material is configured to provide individual responses for each tested target or the target and interferences. That is, the resonant sensor having the sensing material may provide different responses corresponding to each of the analyte. By applying a multivariate analysis (e.g., a principal components analysis), the dimensionality of the complex impedance responses for each of analytes is reduced to a single data point. This processed data is further used for quantitation of targets and their mixtures. As used herein, 'multivariate analysis' refers to an analysis of signals where one or more sensors produce multiple response signals that may or may not be substantially correlated with each other. The multiple response signals from the sensors may be analyzed using multivariate analysis tools to construct response patterns of exposures to different environmental conditions, such as, pressure or temperature. Non-limiting examples of multivariate analysis tools include canonical correlation analysis, regression analysis, nonlinear regression analysis, principal components analysis, discriminate function analysis, multi-dimensional scaling, linear discriminate analysis, logistic regression, or neural network analysis.

In certain embodiments, the complex impedance response of the sensor is a multivariable response because more than one frequency is utilized to measure sensor response. The sensor response is measured at multiple frequencies across the resonance of the sensor. For example, if the sensor resonates at about 13 MHz, the measured frequencies and associated sensor responses are measured from about 5 MHz to about 20 MHz. This multivariable response is analyzed by multivariate analysis. The multivariable response of the sensor includes the sensor's full complex impedance spectra and/or several individually measured properties Fp, Zp, Fz, F1, F2, Z1, and Z2. These properties include the frequency of the maximum of the real part of the complex impedance (Fp, resonance peak position), magnitude of the real part of the complex impedance (Zp, peak height), zero-reactance frequency (Fz, frequency at which the imaginary portion of impedance is zero), resonant frequency of the imaginary part of the complex impedance (F1), and antiresonant frequency of the imaginary part of the complex impedance (F2), signal magnitude (Z1) at the resonant frequency of the imaginary part of the complex impedance (F1), and signal magnitude (Z2) at the antiresonant frequency of the imaginary part of the complex impedance (F2). Other parameters can be measured using the entire complex impedance spectra, for example, quality factor of resonance, phase angle, and magnitude of impedance. Multivariable response parameters are described in U.S. patent application Ser. No. 12/118,950 entitled "Methods and systems for calibration of RFID sensors", which is incorporated herein by reference.

In one embodiment, the RFID tag of the RFID sensor may be a passive tag. A passive RFID tag does not need a battery for its function and comprises a memory chip, which is connected to the reader antenna. In one embodiment, the field-portable impedance reader may be coupled to a finite electrical power source, which is self-contained (i.e., internal) within the field-portable impedance reader, such as a relatively small portable battery consisting of one or more disposable dry cells or rechargeable cells. Alternatively, the field-portable impedance reader may be operable using a power supply that is hard wired to a remote electrical power source, such as an electric grid.

In one embodiment, the impedance reader may be disposed at a determined distance from the RFID sensor to obtain sensor information. In one example, the impedance reader is a short-range micro-communication impedance reader. As used herein, the term "short-range communication" means a near field communication, which is a wireless communication technology which enables the exchange of data between devices which may be either in contact, or at a distance of up to about 1 m. The near field distance may be also expressed in the number of wavelengths of electromagnetic radiation. In one example, the near field may comprise a distance of less than about 10 wavelengths. In another embodiment, the impedance reader may be directly attached to the sensor to obtain sensor information. The distance between the RFID sensor and the impedance reader is governed by the design parameters that include operating frequency, RF power level, writer/reader's receiving sensitivity, antenna dimensions, data rate, communication protocol, and microchip power requirements. The communication distance between the resonant sensor and the impedance reader is typically limited within a proximity distance because the passive tag operates with only microwatts to milliwatts of RF power. For passive tags operating at 13.56 MHz, the read distance is typically not more than several centimeters. With increased RF power of operation, large antenna dimensions, and large sensor dimensions, the read distance may be larger than several centimeters. In one embodiment, the impedance reader may be in wireless communication with a central computing center for analyzing the sensor information obtained by the impedance reader.

In one embodiment, the impedance reader is operated at a minimum output power required for application-driven signal-to-noise ratio. In one example, the components of the impedance reader, such as, but not limited to reader antenna, impedance compensator, calibrator, synchronous sampler, and digital processor, are integrated with low power consumption and are able to operate using a battery source, or an energy-harvesting source. Non-limiting examples of energy-harvesting sources include super-capacitors, sources based on ambient light, sources based on human motion, sources based on industrial vibration, sources based on thermal energy (human and industrial), sources based on radio frequency energy from cell phones.

The field-portable impedance reader may provide sensor information to a central computing center using wireless communication. The field-portable impedance reader may be in communication with the central computing center via a network for processing the digital and analog data. The central computing center may be directly or indirectly coupled to one or more sensors (or neighboring sensors). In this way, the field-portable impedance reader may advantageously have access to information provided by other sensors.

Non-limiting examples of a central computing center include a central hub or a cloud-computing cluster. As used herein, the term "cloud computing" is an Internet-based computing, whereby shared resources, software and information are provided to computers and other devices on-demand. A central processor might be used to generate detailed response models. Cloud computing may reduce the cost and capital expenditure. In addition, cloud computing may provide location independence by enabling the users to access the systems using a web browser regardless of their location or what device they are using (e.g., personal computer, mobile telephone, multi-functional device). In one example, a cloud computing cluster would allow a user or automated system to dynamically evolve the model based on, for example, changing ambient noise parameters. Non-limiting examples of such ambient noise parameters include temperature, humidity and pressure. In some applications, these and other environmental parameters may be parameters of a measurement of interest. Values of ambient noise parameters may be provided from the same or different sensors. The detailed response model may evolve based on neighbor sensors that provide similar types of sensing information or different sensing information about other measured parameters.

In certain embodiments, the field-portable impedance reader of the invention may interrogate analog signals from a plurality of sensors. The plurality of sensors may have similar or different structures depending on the particular environmental parameter that these sensors are designed to sense. In one example, the information from the different sensors may be combined to provide sensor responses corresponding to different environmental parameters. In another example, some sensors may be designed to measure environmental parameters, such as temperature or pressure, while the other sensors may be designed for other applications, such as chemical or/and biological analyte detection.

In one embodiment, a method for quantitating one or more of chemical, biological, or physical parameters in an environment is provided. The method comprises measuring a frequency-dependent impedance response of an LCR sensor across a resonance frequency, using a portable impedance reader, and simultaneously calculating at least two univariate responses from the LCR sensor. In one example, at least two responses from a first sensor and at least one response from a second sensor may be transmitted to a central computing center, where the first and second sensors are disposed in close proximity of each other. In one embodiment, simultaneously calculating comprises wirelessly transmitting the impedance response to a central computing center. A multivariate analysis is performed over the at least two univariate responses from the LCR sensor, and the results of the multivariate analysis are correlated to stored calibration values to provide quantitative values of the measured sensor responses to the parameter levels. In one embodiment, analyzing, correlating, or both are performed in the central computing center. The quantitated values may be wirelessly transmitted back to the field-portable impedance reader. The quantitated values may be displayed on a display screen of the impedance reader.

The analyzing may be performed for steady state or dynamic responses. The steady state sensor response is a response from the sensor over a determined period of time, where the response does not appreciably change over the measurement time. Thus, measurements of steady state sensor response over time produce similar values. The dynamic sensor response is a response from the sensor upon a sudden change in the measured environmental parameter (temperature, pressure, chemical concentration, biological concentration, etc.) Thus, the sensor response does significantly change over the measurement time. Thus, measurements of dynamic sensor response over time produce dynamic signature of response. Non-limiting examples of the dynamic signature of the response include average response slope, average response magnitude, largest positive slope of signal response, largest negative slope of signal response, average change in signal response, maximum positive change in signal response, and maximum negative change in signal response.

Figure 1:
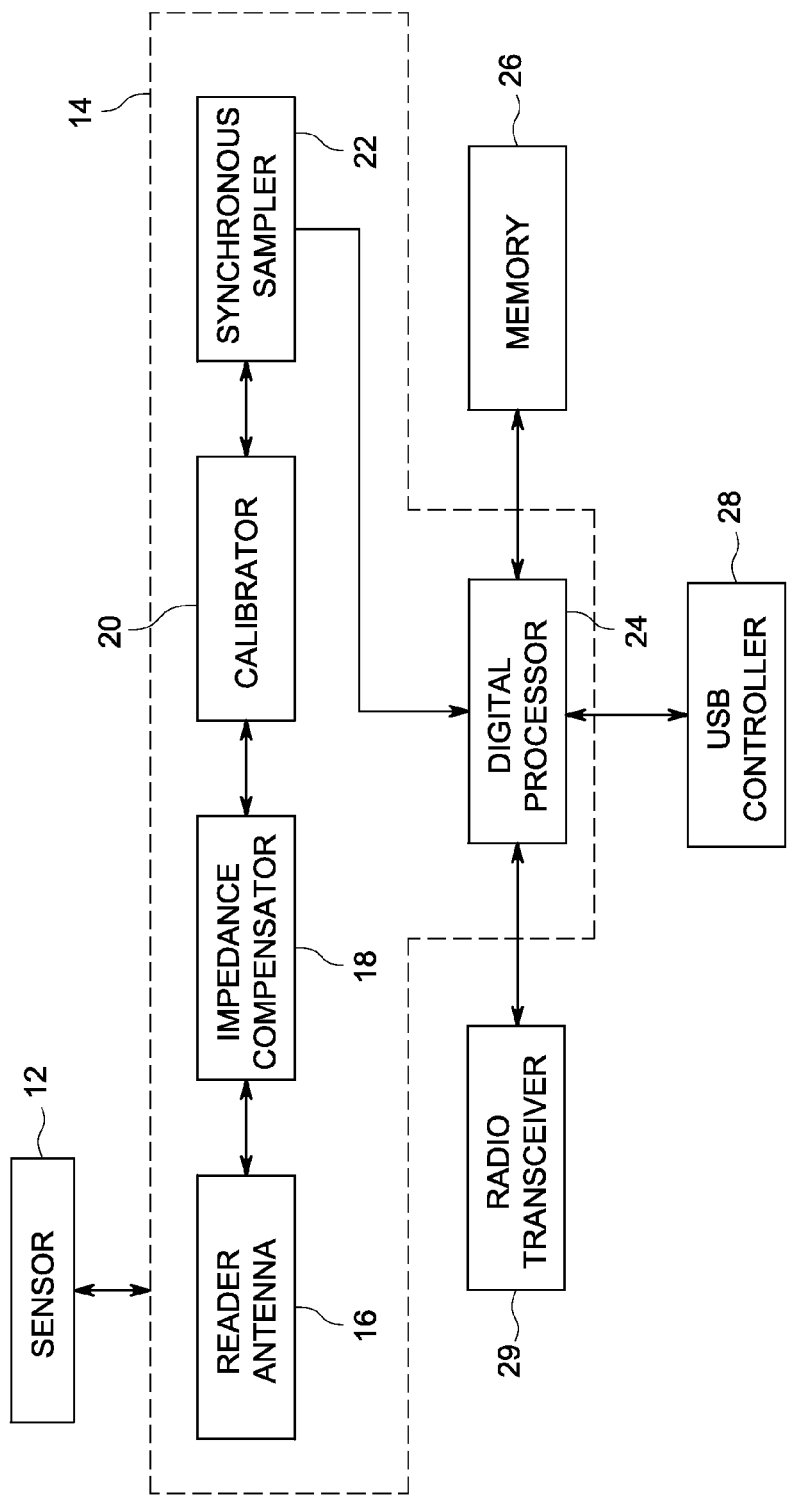
FIG. 1 is a schematic view of an example of a field-portable impedance reader for measurements of resonance impedance of a resonant sensor.

FIG. 1 illustrates an example of a system 10 having a resonant sensor 12 in close proximity to a field-portable impedance reader 14. In one example, the sensor 12 comprises a passive RFID tag with integrated circuit read/write memory chips operating at 13.56 MHz. The field-portable impedance reader 14 is configured for measurements of resonance impedance response of the RFID sensor 12 in proximity communication to the reader 14 or electrically directly connected (for example, using wires) to the impedance reader 14. The sensor 12 is operatively coupled to a reader antenna 16. The reader antenna 16 is also known as a sensor pick-up coil. The reader antenna 16 inductively couples the sensor 12 to the impedance reader 14. The reader antenna 16 may or may not be part of the impedance reader 14. Optionally, a reader for reading a digital portion of the resonant sensor 12 may be incorporated into the impedance reader 14.

An impedance compensator 18 may be operatively coupled to the reader antenna 16. In one example, the impedance compensator 18 may be a matching transformer. The impedance compensator 18 may be used to match the impedance of the calibrator 20 to the combined impedance of the resonant sensor 12 and the reader antenna 16. The impedance compensator 18 enables efficient transfer of energy between the reader antenna 16 and the calibrator 20. In addition, the impedance compensator 18 minimizes power losses in the system 10. The impedance compensator 18 may include components, such as but not limited to, a matching transformer, a resistive bridge, or an active circuit such as a generalized impedance converter (GIC).

Although not shown, optionally, the impedance compensator 18 may include a temperature compensator. For example, temperature often has an undesirable effect on the sensor 12 or on the reader antenna 16. To minimize these effects, an independently-measured temperature may be used in the behavioral model.

The calibrator 20 may be used to calibrate the sensor signals, and to verify the proper operation of the impedance reader 14. The calibrator 20 may comprise a switch for calibration standards. The calibrator 20 may comprise an open loop or a closed loop LCR circuit. The calibrator 20 is used to provide a stable calibrated reference for measured parameters to reduce or prevent undesirable sensed parameters from negatively affecting the measurements and to improve accuracy of sensing. The calibrator 20 may also function as an internal self-test, notifying the operator of device faults. Non-limiting examples of undesirable sensed parameters include temperature and aging. In one example, aging may include corrosion of traces on the circuit board.

The calibration of the sensor signals enables accurate measurements of one or more parameters of interest to which the sensor 12 is exposed through changes in the impedance response of the sensor 12. In one embodiment, the calibrator 20 may enable the sensor 12 to be self-calibrated without first exposing the sensor 12 to the parameter of interest. In one example, self-calibration may be performed by measuring the impedance response of the sensor 12, comparing the impedance response of the sensor 12 to reference impedance values and extracting equivalent circuit parameters of the sensor.

In one example, the method of calibration of the impedance reader 14 may include measuring impedance of a reference structure as a function of frequency and comparing measured values with values stored in the non-volatile memory of the reader. Non-limiting examples of the reference structure may include one or more of a reference resistor, a reference capacitor, a reference inductor, or a reference LCR circuit. In one example, a built-in switch (not shown) may be provided in the impedance reader 14 for calibration. In one example, the method of calibrating the sensor may comprise measuring the impedance of an sensor, relating the measurement of impedance of the sensor to one or more parameters, computing one or more analytical fit coefficients, and storing the one or more analytical fit coefficients on a memory chip of the sensor or in any other known location.

The impedance reader 14 further comprises a synchronous sampler 22. The synchronous sampler 22 receives calibrated sensor signals from the calibrator 20, and references the calibrated sensor signals against reference signals obtained from a reference source. In one example, the reference source is a set of signals employed for referencing sensor response. In one embodiment, referencing comprises normalizing. However, any other functions typically used for referencing may also be used. In one embodiment, the synchronous sampler 22 may generate one or more reference signals that may be used for referencing the sensor signals. In one embodiment, the reference signals produced by the synchronous sampler 22 may act as excitation signals for the calibrator 20 to obtain a response from the calibrator 20. The synchronous sampler 22 may be constructed using a direct sampling architecture, a heterodyne sampling architecture, a homodyne sampling architecture, or a sub harmonic sampling architecture.

The synchronous sampler 22 may comprise a master oscillator, a coherent clock generator, and/or a digital direct synthesizer (DDS). In one example, the master oscillator may be independent from the coherent clock generation circuit. In another example, the master oscillator and the coherent clock generator may be integrated with the DDS. The DDS may receive $f_{DDSclk}$ as an input to produce reference frequency ($f_1$) and a sample frequency ($f_2$). The frequencies $f_1$ and $f_2$ are coherent (same phase) with the $f_{DDSclk}$. In one embodiment, a duty-cycled operation may be implemented to minimize average power while maintaining an appropriate sensor-sampling rate. The duty cycling approach provides stability similar to reference designs stability of measurements as well as the period between sampling intervals.

The frequency difference between $f_1$ and $f_2$ may be maintained constant to digitally perform demodulation. This frequency relationship (constant frequency difference), and phase coherency enables suppression of external electromagnetic interference by averaging out signals that are not synchronous or phase-locked to the master oscillator. Optionally, the output from the DDS is first passed through a filter, such as a low pass filter (not shown) to remove unwanted spurious outputs from the DDS. The filtered output may be passed through an amplifier (not shown) to increase signal levels to provide a suitable excitation signal level for carrying out the impedance measurements of the RFID sensor.

The DDS may be swept over the desired measurement frequency range. In one embodiment, the DDS may be swept in a step-wise fashion. In one embodiment, a swept frequency analyzer may be used to increase the frequency of the master oscillator, such that the difference between the frequency of the swept frequency analyzer, and the master oscillator is within a bandwidth of an intermediate-frequency filter. The frequency signals from the DDS may be used as excitation signals for a reader antenna. Upon being excited by the excitation signals from the DDS, the reader antenna 16 generates magnetic field to interact with the sensor 12.

The synchronous sampler 22 is coupled to a digital processor 24. In one example, the digital processor 24 is a digital signal processor (DSP). In another example, the digital processor 24 is an ADC. In one embodiment, an additional ADC may be used to convert analog signals from the sensor 12 into digital signals. The digital signals may be then processed using the digital processor 24.

In one embodiment, the digital processor 24 may comprise a complex digital demodulator (DDM) to avoid typical distortion issues with analog quadrature demodulation. The DDM may be simplified by having the frequency difference of the calibrated sensor signals and the reference signals to be a known fraction (such as one fourth) of a sample clock. The output of the digital processor 24 may be the ratiometric amplitude and the phase difference of the calibrated sensor signal and the reference signal. Although not shown, the digital processor 24 may also include a Fast Fourier Transform (FFT) matched filter to enhance signal to noise ration of the reader 14 by coherently accumulating desired signals while rejecting out-of-band interference signals.

In one embodiment, the digital processor 24 may be operatively coupled to a memory 26 for storing measurement parameters for later use, or displaying the measurement parameters, or downloading the measurement parameters for further analysis and/or transferring the measurement parameters to a central computing unit. The digital processor 24 may have adaptors for coupling the device to external systems such as a remote computing unit (also referred to as "central computing center"). In one example, the digital processor 24 may have a USB controller 28 to provide USB interface. The USB interface enables the impedance reader 10 to be updated and further enables data to be collected in the field and then downloaded for further analysis. In another example, the digital processor 24 may have a wireless communication means, such as a radio transceiver 29 to wirelessly communicate with external systems. For example, the field-portable impedance reader 14 may be operatively coupled to a communication module. The communication module may be used to communicate with external devices, such as a network.

In certain embodiments, a display (not shown) may be operatively coupled to the digital processor 24. In one embodiment, a high contrast color transreflective LCD (liquid crystal display) graphic displays may be used as a display. The high contrast and transreflective nature of the display makes the display suitable for outdoor daylight operation in the field.

In an alternate embodiment, instead of, or in addition to, using the digital processor 24, the impedance reader 14 may employ a remotely located processor. For example, the remotely located processor may be present in a remotely located central computing center with respect to the impedance reader 10. In addition to processing the sensor data (analog and digital data), the digital processor 24 may be configured to display the processed data.

In certain embodiments, the field-portable impedance reader 14 may be disposed in a compact housing (not shown). For example, the field-portable impedance reader 14 may be disposed in a suitable rectangular box-shaped housing having dimensions in a range from about 2×2×1 cm$^3$ to about 15×15×5 cm$^3$. The housing may comprise handle, pin, or provisions for straps to facilitate easy carrying of the device to various locations. A display may be disposed in a window within the housing. The resonant sensor 12 may be disposed either on or outside the housing.

The impedance reader 14 measures impedance spectrum of a resonant sensor circuit of the sensor 12. In addition, analysis of the measured spectrum may be performed in the impedance reader 14. Alternatively, analysis may be performed in a central networked location after sending the collected impedance spectrum to the central networked location. Non-limiting examples of analysis of spectrum includes frequency of the maximum of the real part of the complex impedance (Fp), magnitude of the real part of the complex impedance (Zp), resonant frequency of the imaginary part of the complex impedance (F1), and anti-resonant frequency of the imaginary part of the complex impedance (F2).

Figure 2:
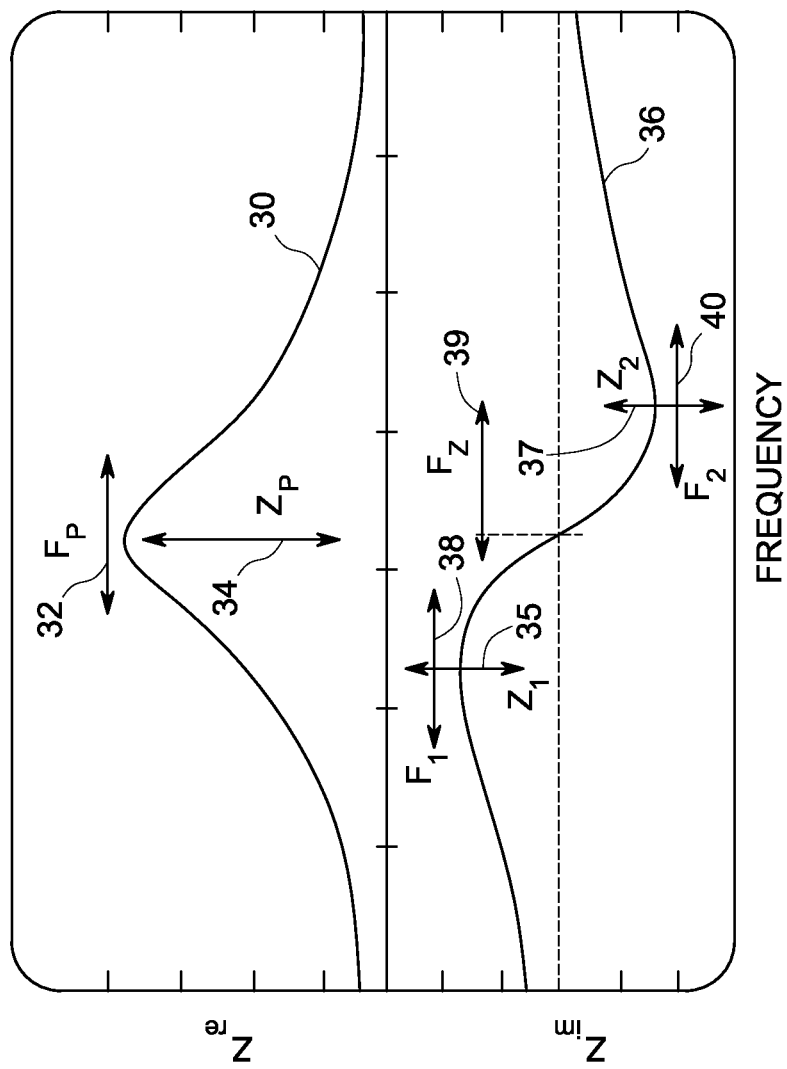
FIG. 2 is a graph of simultaneously measured impedance parameters of an embodiment of the resonant sensor of the invention.

The combination of components of sensor circuit result in the generation of an impedance response formed by resonant circuit parameters such as $F_p$, $Z_p$, $F_1$, $F_2$, Fz, $Z_1$, $Z_2$ and some others produced simultaneously from the resonant sensor. FIG. 2 illustrates examples of real and imaginary portions of the impedance of the sensor. As illustrated by the curve 30, the real part of the impedance includes parameters $F_p$ 32 and $Z_p$ 34. The parameter $F_p$ 32 represents the frequency of the maximum of the real part of the impedance, and the parameter $Z_p$ 34 represents the magnitude of the real part of the impedance. Similarly, as illustrated by the curve 36, the imaginary part of the impedance includes $F_1$ 38 and $F_2$ 40. The parameter $F_1$ 38 represents resonant frequency of the imaginary part of the impedance, and the parameter $F_2$ 40 represents anti-resonant frequency of the imaginary part of the impedance. The parameters $F_1$ and $F_2$ are related to different components of the equivalent circuit. Additional non-limiting examples of the sensor parameters include parameters that can be extracted from the response of the equivalent circuit of the RFID sensor, for example, the quality factor of resonance, phase angle, and magnitude of impedance of the resonance circuit response of the RFID sensor, and others known in the art. The difference between $F_1$ 38 and $F_2$ 40 is related to peak width. In this example, since $F_1$ 38 and $F_2$ 40 are related to different components of an equivalent circuit, $F_1$ 38 and $F_2$ 40 are not correlated. Peak symmetry may be affected by changes in impedance. Other parameters can be measured using the entire impedance spectrum, for example, using the quality factor of resonance, phase angle, and magnitude of impedance, signal magnitude ($Z_1$) 35 at the resonant frequency of the imaginary part of the complex impedance ($F_1$) 38, signal magnitude ($Z_2$) 37 at the antiresonant frequency of the imaginary part of the complex impedance ($F_2$) 40, and zero-reactance frequency (Fz, frequency at which the imaginary portion of impedance is zero) 39. Multivariable response parameters are described in U.S. patent application Ser. No. 12/118,950 entitled, "Methods and systems for calibration of RFID sensors", which is incorporated herein by reference.

In certain embodiments, the field-portable reader may comprise additional features and functions and controllable features that may or may not be needed for field applications. Non-limiting examples include variable gain and programmable gain amplifiers and an operation capability over broad frequency range.

Components that are sensitive to drift during power cycling and warm-up, such as the impedance converter and the calibrator, may operate in a low power, but not completely off, mode to preserve measurement performance and accuracy. Less sensitive components, such as the synchronous sampler and digital processor, are completely powered off during duty cycle sleep intervals to save power. This method affords reduced power consumption and allows power savings by decreasing the duty cycle of operation. Other examples for saving power may include the use of multiple channel DDS chips and multiple channel ADC converters to provide savings by being able to use the common parts such as time-bases, counters, memories, and interface controllers.

In one embodiment, the field-portable impedance reader may use a battery for power supply. In one example, the battery may be a standard rechargeable lithium ion battery. Lithium ion batteries have favorable energy/weight ratios and no memory effects. In one embodiment, the lithium ion battery may be able to provide power for duration of about 13.5 hours at one measurement per minute, and with 15 percent duty cycle.

In one example, the field-portable impedance reader measures the impedance, amplitude and phase of the resonant sensor response over a frequency range from about 8 MHz to about 15 MHz. In this example, the field-portable impedance reader comprises a master oscillator and coherent clock generation circuit, a direct digital synthesizer (DDS), down conversion mixers and filters, analog to digital conversion and a digital signal processor. The reader architecture also contains a USB interface for local communication and battery charging as well as a 802.15.4 ZigBee radio transceiver.

Figure 3:
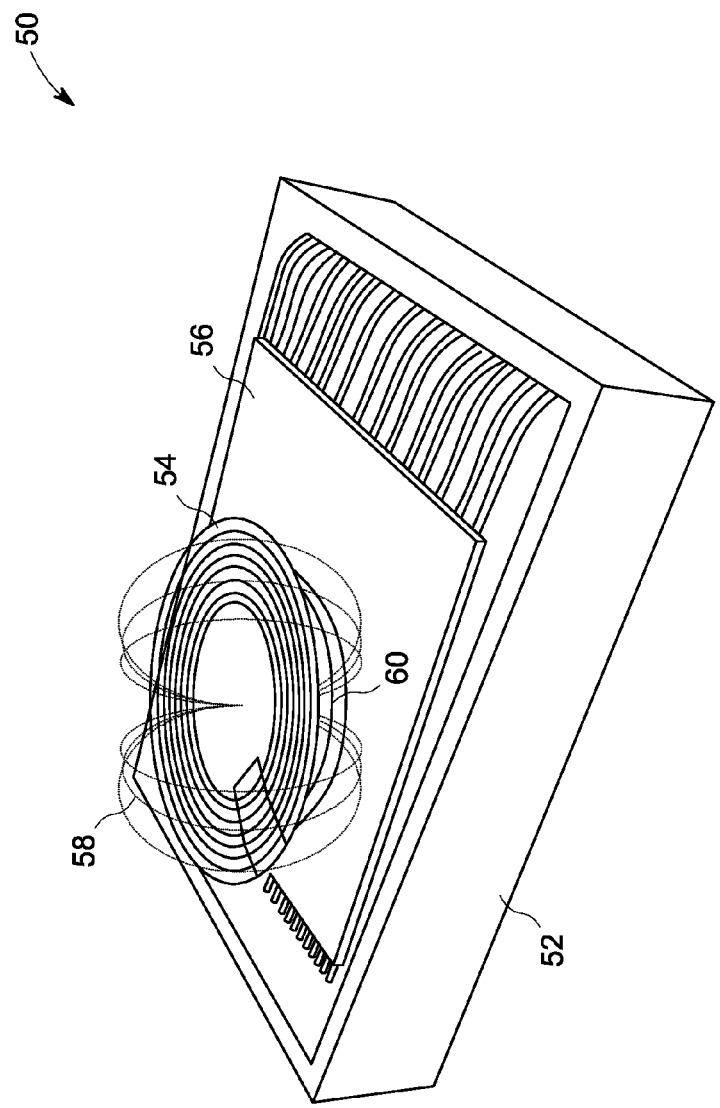
FIG. 3 is a perspective view of an example of a field-portable impedance reader for a resonant sensor.

FIG. 3 illustrates a field-portable impedance reader 50. In the illustrated embodiment, components of the impedance reader 50 are disposed in a portion of a housing 52. A RFID sensor 54 is disposed on a circuit board 56. A magnetic field 58 is generated from the reader antenna 60.

Figure 4:
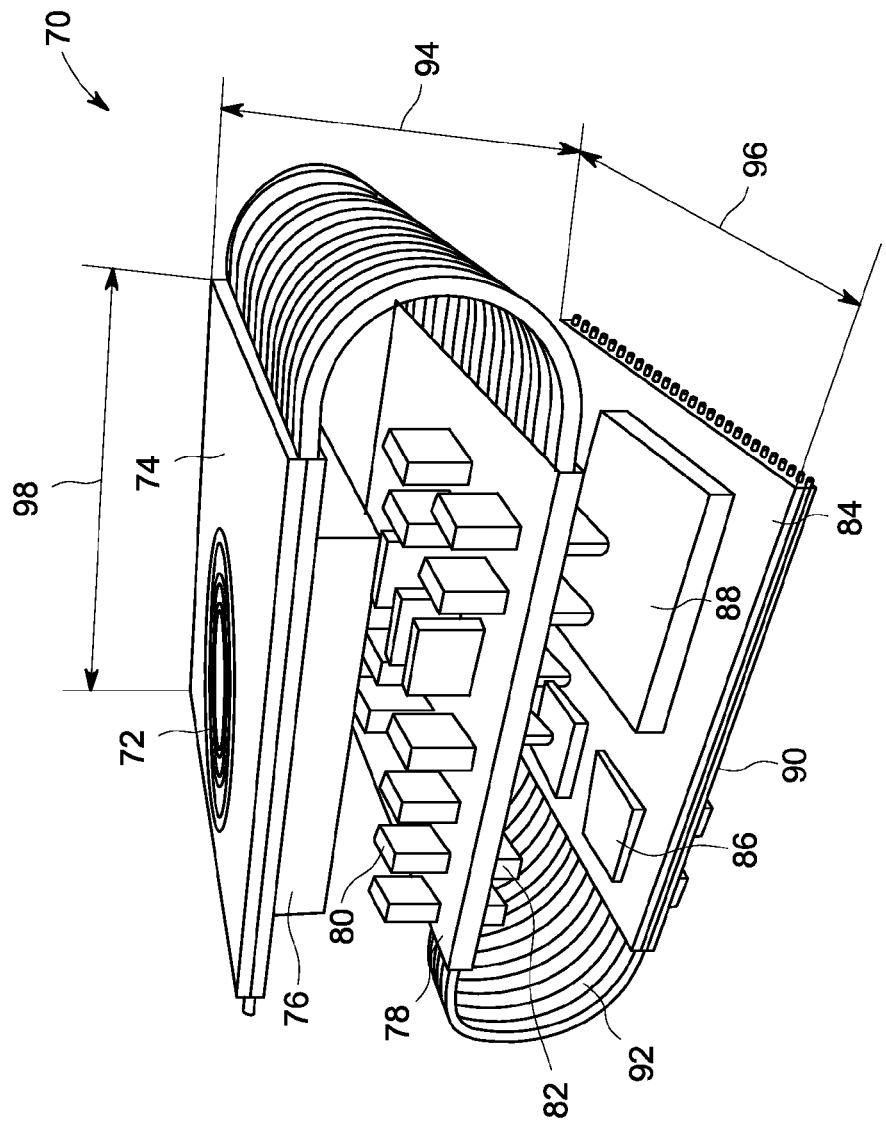
FIG. 4 is a perspective view of an example of a field-portable impedance reader employing surface mount components on a rigid-flex double circuit board.

FIG. 4 illustrates detailed structure of an example structure of a field-portable impedance reader 70. In the illustrated example, a double-sided surface-mount design approach is used. However, other approaches, such as, but not limited to, connectorized components or through-hole components may also be used. A rigid flex-based board stacking is used to support various components of the impedance reader 70. The surface mount components on a rigid-flex double circuit board are folded and stacked for small form factor.

A first rigid circuit board 74 has a reader antenna 72 disposed on one side. The reader antenna 72 is designed to operate in the frequency band in a range from about 5 MHz to about 100 MHz. While a horizontal coil antenna is illustrated, other antenna types, including dipoles, verticals, etc., may be used.

A rechargeable or replaceable battery 76 is disposed on opposite side of the rigid circuit board 74. Non-limiting examples of the battery may include a lithium ion battery or an alkaline battery. A second rigid circuit board 78 includes radio frequency (RF) electronics 80 on one side, and intermediate frequency (IF) electronics 82 on the other side. A third rigid circuit board 84 comprises ADC 86 and DSP 88 on one side, and USB and/or radio antenna 90 on the other side. The different rigid circuit boards 74, 78 and 84 are electronically coupled using flex bend interconnect 92. Disposing the electronics in stacked form helps miniaturize the reader 50.

Although not shown, other configurations of the electrical components of the impedance reader 70 are also envisioned. For example, instead of being disposed on three layers circuit boards, the electrical components may be disposed on one or two layers of circuit boards. The electrical components may be disposed on several layers of circuit boards ranging from 1 to about 10 layers.

The inductively coupled approach allows the galvanic isolation (no wires) of the sensor and the reader and permits a rapid snap-on of a desired passive RFID sensor onto the surface of the sensor reader. If needed, a simple exchange of the passive RFID sensors may be performed.

Figure 5:
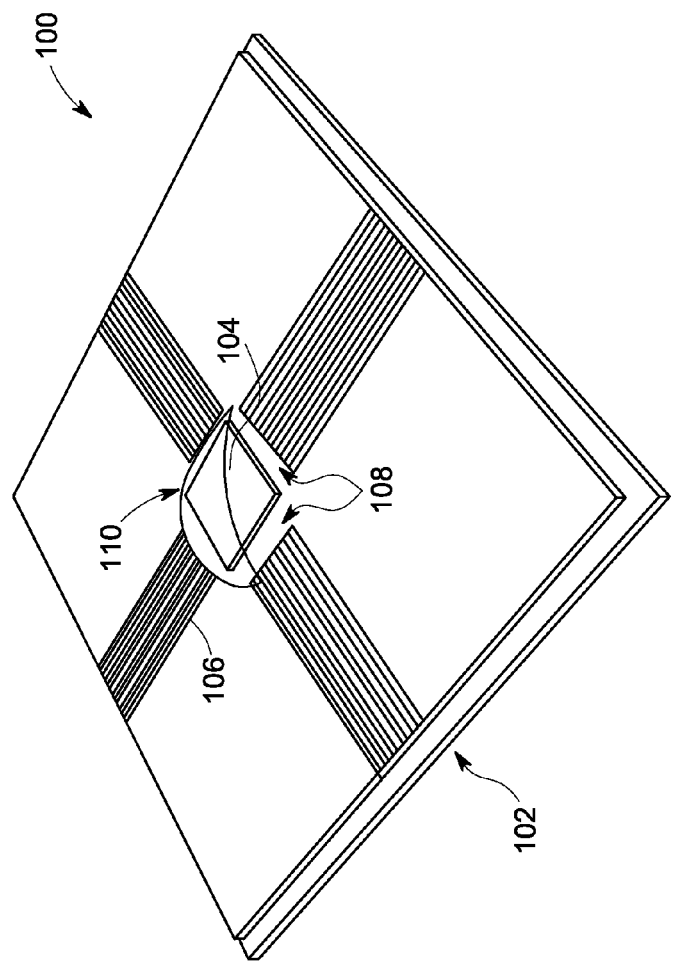
FIG. 5 is a perspective view of an example of glob tops approach for electronic packaging of component of a field-portable impedance reader.

Referring to FIG. 5, miniaturization of the field-portable impedance reader may be optimized by using electronics assembly techniques. One of the challenges in achieving small electronics lies in the hierarchy of packaging techniques and interconnection methods used throughout the manufacturing and handling process. In addition to the size of the packages, thermal issues as well as cross-couplings between sensitive circuits are reduced or eliminated by using a suitable layout. In the illustrated embodiment, the IC chips are directly bonded with glob tops to eliminate issues with large size packages. As illustrated, a silicon die 102 is glued to the circuit board 104 and interconnects are made from the circuit board to the chip using substrate pads 106 and wire bonds 108. For stability, the chip and corresponding wire bonds 108 are encapsulated using a drop, or glob 110, of epoxy. The glob top approach significantly reduces the surface area needed for the component in addition to providing a lower profile, thinner assembly. Also, the glob top approach provides mechanical support and excludes contaminants such as fingerprint residues that could disrupt circuit operation. Other interconnection methods may be used instead of wire bonding, such as but not limited to, a flip-chip die attach with solder reflow or thermosonic bonding. In certain embodiments, the field-portable impedance reader at least maintains the same quality of the data acquisition as conventional desktop laboratory systems.

In certain embodiments, the field-portable impedance reader may interrogate the resonant sensor decode and transmit the measurements to a device. Optionally, the field-portable impedance reader may record the decoded measurements. The decoded measurements may be transmitted to a local base station or a remote location. In one example, the decoded measurements may be transmitted using a ZigBee® protocol. The architecture contains a USB interface for local communication and battery charging as well as an 802.15.4 ZigBee® radio transceiver for low-power communication approach.

In one embodiment, frequency response measurements are taken by scanning frequencies over a determined range. In another embodiment, frequency response measurements are taken by exciting all frequencies in a determined range. Next, a Fourier transform of the ring-down signal is determined.

The impedance reader is capable of determining sensor parameters while maintaining low noise levels. The spectrum parameters are determined, with minimized uncertainty for further multivariate analysis, in part, by scanning the frequency range with a constant predetermined resolution. The number of waveforms may range from 1 to 10000, and the number of scans may range from 1 to 10000. The waveforms may be averaged if the number of waveforms is more than 2. Scans may be averaged if the number of scans is more than 2. A function may be applied to fit the resonance portion of the scan. In one embodiment, the function may be applied to fit the resonance portion of the scan that comprises 35 percent or less of the total data points in the scan. Peak positions and magnitude of the peaks may be extracted using the function. Non-limiting examples of functions include polynomial fits and centroid fits. Impedance spectrum may be measured with the constant or variable scan speed across a frequency range. The variable scan speed across the frequency range may be used to reduce measurement noise while scanning over a resonance frequency range. Impedance spectrum may be measured with a constant or variable scan frequency resolution across the frequency range. The variable frequency resolution across frequency range may be used to reduce measurement noise over scanning over a resonance frequency range.

The impedance reader of the invention is capable of reading the resonance impedance spectra of resonant sensors using a portable device. For example, one or more embodiments of the portable devices use inductive coupling and a readout of the sensor response, scanning frequency ranges across sensor narrow resonance response, processing of resonance spectra to provide higher resolution and higher signal-to-noise ratio of determinations of peak position and peak intensity, and collecting the resonance impedance spectra of resonance sensors. In one example, the impedance reader has the ability to wirelessly transfer data to one or more cloud computer clusters for cost-effective processing. In another example, the impedance reader comprises the ability to wirelessly adjust the sensor model based on neighboring sensors, in part, by using the data from the neighbor sensors. The data from the neighboring sensors may be transmitted to the impedance reader through the network. In one example, the impedance reader may be a part of a wireless system. Non-limiting examples of the wireless system may comprise a personal computer, a personal digital assistant (PDA), a cellular phone, or a combination device.

Example 1

Measurements were done using a network analyzer to determine the best data acquisition conditions that minimize the noise level in measurements of resonance spectra of developed sensors. The collected complex impedance data was analyzed using Excel (MicroSoft Inc. Seattle, Wash.) or KaleidaGraph (Synergy Software, Reading, Pa.) and PLS_Toolbox (Eigenvector Research, Inc., Manson, Wash.) operated with Matlab (The Mathworks Inc., Natick, Mass.).

Figure 6A:
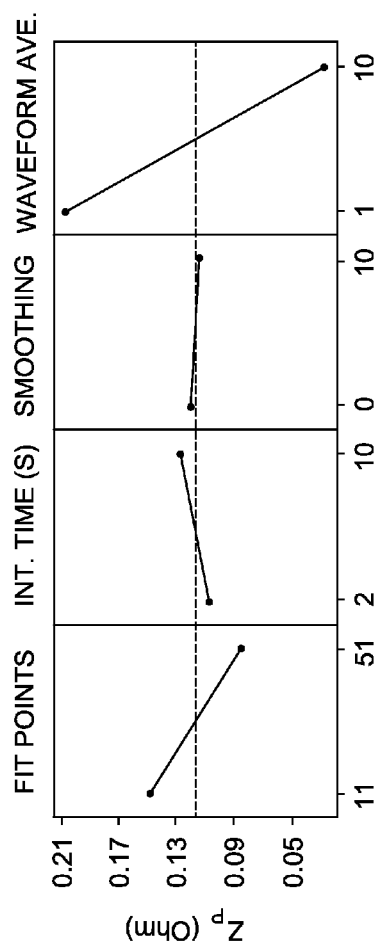
FIGS. 6A and 6B are graphs of an example of a method to determine data acquisition conditions to minimize the noise level.
Figure 6B:
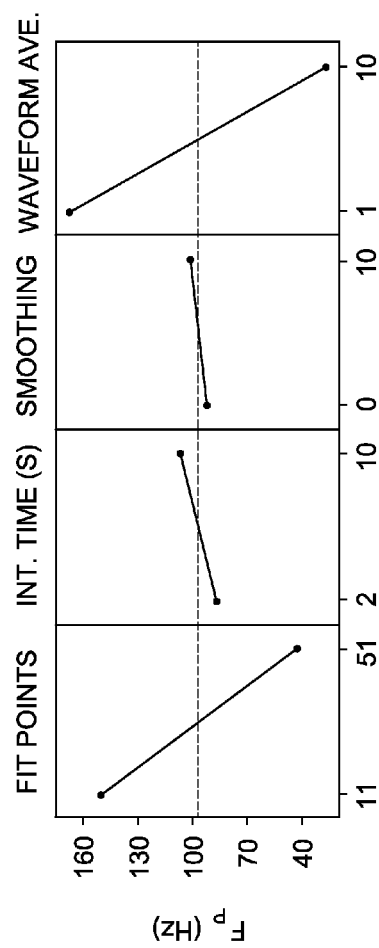

The variable data acquisition parameters included (1) number of fit points across the resonance peak that are used to calculate the peak position, (2) integration time, (3) percent smoothing of spectra, and (4) number of waveforms that are used for averaging. FIGS. 6A and 6B illustrate suitable data acquisition conditions to minimize the noise level. FIG. 6A is the measured Zp, and FIG. 6B is the measured Fp. As shown in FIGS. 6A and 6B, the parameter that improved the noise was the number of waveforms that are used for averaging, followed by the number of fit points across the resonance peak that are used to calculate the peak position. This finding was critical for the reduction of the noise in measurements for achieving the best detection limits in sensor response.

Figure 7:
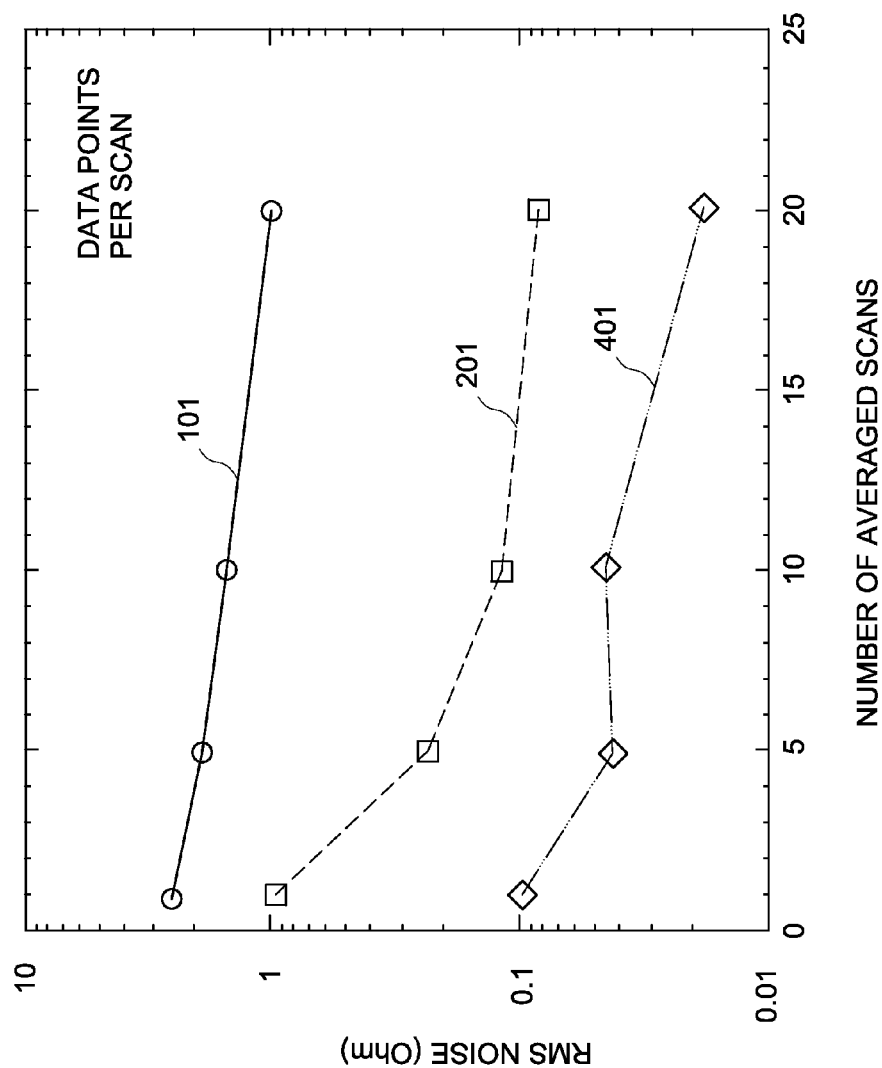
FIG. 7 is a graph of examples of improvement in the noise of an embodiment of the impedance reader, at least in part, by optimizing the number of data points per scan and the number of averaged scans.

FIG. 7 illustrates the improvement in the noise of the network analyzer by optimizing the number of data points per scan and the number of averaged scans.

Example 2

Measurements of three different types of vapors, water, methanol and ethanol, were done using a portable network analyzer. The collected complex impedance data was analyzed using Excel (MicroSoft Inc. Seattle, Wash.) or Kaleida-Graph (Synergy Software, Reading, Pa.) and PLS_Toolbox (Eigenvector Research, Inc., Manson, Wash.) operated with Matlab (The Mathworks Inc., Natick, Mass.). The sensor was a wireless sensor coated with Au nanoparticles. Tested vapors were water, methanol, and ethanol, at four concentrations each. From the collected complex impedance, several parameters were measured simultaneously. These parameters included Fp, Fz, F1, F2, Zp, $Z_1$ and $Z_2$. FIGS. 8A and 8B illustrates graphs during operation of the field-portable impedance reader that was used to conduct measurements from a single sensor that discriminated between the three different types of vapors. FIG. 8A illustrates simultaneously measure Fp, Fz, $F_1$, and $F_2$. FIG. 8B illustrates simultaneously measured Zp, $Z_1$ and $Z_2$.

FIGS. 9A and 9B illustrate scores plots from the principal components analysis performed during operation of the field-portable impedance reader that was used to conduct measurements from a single sensor that discriminated between the three different types of vapors. FIG. 9A illustrates scores plot of principal component 1 (PC1) with respect to principal component 2 (PC2). FIG. 9B illustrates scores plot of principal component 1 (PC1) with respect to principal component 2 (PC1) and experiment time. Principal components analysis was performed on simultaneously measured responses Fp, Fz, $F_1$, $F_2$, Zp, $Z_1$ and $Z_2$ from a single sensor. This example demonstrated the operation of the portable network analyzer in the selective determination of three vapors.

Example 3

A field-portable impedance reader that measures complex impedance was tested for its battery operation. The field-portable impedance reader was built in its double-sided, surface mount configuration. The impedance reader operated in a continuous mode and 15 percent duty cycle on a Li-ion rechargeable battery (Ultralife UBP001, 3.7V, 1750 mAh) communicating by wireless (ZigBee) in real-time. Upon detailed testing of assembled components of the portable system, the noise characteristics and the ability for selective detection of multiple vapors were comparable with the desktop network analyzer. The packaged system comprising the field-portable impedance reader achieved 13.5 h of battery operation.

While only certain features of the invention have been illustrated and described herein, many modifications and changes will occur to those skilled in the art. It is, therefore, to be understood that the appended claims are intended to cover all such modifications and changes as fall within the scope of the invention.

The invention claimed is:

1. A field-portable impedance reader, comprising:
   a first layer comprising a reader antenna;
   a second layer comprising radio frequency electronics and intermediate frequency electronics; and
   a third layer comprising a digital direct synthesizer, a reference analog to digital converter, a sample analog to digital converter, and a digital signal processor,
   wherein the first, second and third layers are disposed in a housing.

2. The field-portable impedance reader of claim 1, wherein the third layer further comprises a synchronous sampler, and wherein the synchronous sampler comprises a master oscillator, a coherent clock generator, or both.

3. The field-portable impedance reader of claim 2, wherein the digital direct synthesizer is in communication with the master oscillator, the coherent clock generator, or both.

4. The field-portable impedance reader of claim 1, wherein the digital direct synthesizer is in communication with the reader antenna.

5. The field-portable impedance reader of claim 1, wherein the digital signal processor comprises the reference analog to digital converter and the sample analog to digital converter.

6. The field-portable impedance reader of claim 1, wherein the field-portable impedance reader is configured to monitor sensing data in real-time.

7. The field-portable impedance reader of claim 1, wherein the field-portable impedance reader is inductively coupled to a resonant sensor.

8. The field-portable impedance reader of claim 7, wherein the field-portable impedance reader is configured to read real and imaginary impedance spectra of the resonant sensor.

9. The field-portable impedance reader of claim 7, wherein the field-portable impedance reader is configured to read real and imaginary impedance spectra of the resonant sensor and simultaneously calculate at least two parameters of a sensor impedance response.

10. The field-portable impedance reader of claim 7, wherein the field-portable impedance reader is configured to read real and imaginary impedance spectra of the resonant sensor and configured to simultaneously calculate $F_p$, $F_z$, $F_1$, $F_2$, $Z_p$, $Z_1$, and $Z_2$ from the resonant sensor.

11. The field-portable impedance reader of claim 1, wherein a surface of the field-portable impedance reader comprises an adaptor is configured to receive a resonant sensor.

12. The field-portable impedance reader of claim 11, wherein the resonant sensor is a passive radio frequency identification (RFID) sensor.

13. The field-portable impedance reader of claim 1, wherein the digital signal processor is in operative association with a memory, a controller, a radio transceiver, or combinations thereof.

14. The field-portable impedance reader of claim 1, further comprising a temperature compensator.

15. The field-portable impedance reader of claim 14, wherein the temperature compensator is integral with an impedance compensator disposed in the third layer.

16. The field-portable impedance reader of claim 1, further comprising a glob top.

17. The field-portable impedance reader of claim 1, further comprising a universal serial bus (USB) interface.

18. The field-portable impedance reader of claim 1, wherein dimensions of the housing are in a range from about 2×2×1 cm$^3$ to about 15×15×5 cm$^3$.

19. A wireless system, comprising a field-portable impedance reader of, wherein the field-portable impedance reader comprises:
- a first layer comprising a reader antenna;
- a second layer comprising radio frequency electronics and intermediate frequency electronics; and
- a third layer comprising a digital direct synthesizer, a reference analog to digital converter, a sample analog to digital converter, and a digital signal processor,
- wherein the first, second and third layers are disposed in a housing.

20. The wireless system of claim 19, further comprising a portable digital device comprising a portable computer processor, a handheld digital assistant, a cellular phone, or combinations thereof.

21. The wireless system of claim 20, wherein the portable digital device is capable of near-field communications.

\* \* \* \* \*